(12) United States Patent
Dexter et al.

(10) Patent No.: US 7,465,717 B2
(45) Date of Patent: Dec. 16, 2008

(54) PROCESS FOR RELEASING AND EXTRACTING PHOSPHATIDES FROM A PHOSPHATIDE-CONTAINING MATRIX

(75) Inventors: Lee Dexter, Austin, TX (US); Roger Peterson, Clarks Grove, MN (US); Udaya Nayanakontha Wanasundara, Saskatoon (CA); Herve Marie Douce, Saskatoon (CA); Thomas Stevenson, Saskatoon (CA)

(73) Assignee: SoyMor, Albert Lea, MN (US)

( * ) Notice: Subject to any disclaimer, the term of this patent is extended or adjusted under 35 U.S.C. 154(b) by 0 days.

(21) Appl. No.: 10/950,838

(22) Filed: Sep. 27, 2004

(65) Prior Publication Data

US 2006/0068041 A1 Mar. 30, 2006

(51) Int. Cl.
*A01N 57/26* (2006.01)
*A01N 65/00* (2006.01)
*A01N 61/00* (2006.01)
*A61K 31/685* (2006.01)
*A61K 36/48* (2006.01)
*A61K 31/00* (2006.01)

(52) U.S. Cl. .............................. 514/78; 424/757; 514/1

(58) Field of Classification Search .................. 987/233
See application file for complete search history.

(56) References Cited

U.S. PATENT DOCUMENTS

| | | | |
|---|---|---|---|
| 2,724,649 A | 11/1955 | Julian et al. | |
| 3,739,047 A | 6/1973 | Stanford et al. | |
| 4,235,793 A | 11/1980 | Betzing | |
| 4,425,276 A | 1/1984 | Gunther | |
| 4,465,693 A | 8/1984 | Strauss et al. | |
| 4,496,486 A | 1/1985 | Gunther | |
| 4,496,489 A | 1/1985 | SenGupta | |
| 4,698,185 A | 10/1987 | Dijkstra et al. | |
| 4,714,571 A | 12/1987 | Tremblay et al. | |
| 4,814,111 A | 3/1989 | Kearns et al. | |
| 5,084,215 A | 1/1992 | Kearns et al. | |
| 5,214,171 A * | 5/1993 | Dijkstra et al. | ................. 554/83 |
| 6,140,519 A | 10/2000 | Hutton et al. | |
| 6,645,742 B2 * | 11/2003 | De Ferra et al. | ............. 435/116 |
| 2003/0219473 A1* | 11/2003 | Zarif et al. | ................... 424/450 |

FOREIGN PATENT DOCUMENTS

| | | |
|---|---|---|
| EP | 0090454 | 3/1983 |
| GB | 412224 | 6/1934 |
| GB | 877031 | 9/1961 |
| GB | 1217846 | 12/1970 |
| GB | 1350390 | 4/1974 |

OTHER PUBLICATIONS http://web.archive.org/web/*/http://www.wpbschoolhouse.btinternet.co.uk/page03/AcidsBasesSalts.htm (Web Publication Date: Feb. 12, 2002). Date Accessed: Oct. 14, 2007.*
http://web.archive.org/web/*/http://www.jtbaker.com/msds/englishhtml/C0357.htm (Web Publication Date: Sep. 12, 2003). Date Accessed: Oct. 14, 2007.*
http://web.archive.org/web/*/http://www.redbirdservice.com/catalog23/solutions%20c.htm (Web Publication Date: Apr. 24, 2003). Date Accessed: Oct. 14, 2007.*

* cited by examiner

*Primary Examiner*—Michele C. Flood
*Assistant Examiner*—Amy L. Clark
(74) *Attorney, Agent, or Firm*—Sherrill Law Offices, PLLC

(57) ABSTRACT

A process for releasing and extracting phosphatides from a phosphatide-containing matrix. The process includes (i) contacting the phosphatide-containing matrix with a solvent and a metal salt to release phosphatides from the matrix and form a phosphatide enriched solvent portion and a phosphatide depleted matrix portion, (ii) separating the phosphatide enriched solvent portion from the phosphatide depleted matrix portion, and (iii) recovering the phosphatides from the phosphatide enriched solvent portion.

22 Claims, No Drawings

PROCESS FOR RELEASING AND EXTRACTING PHOSPHATIDES FROM A PHOSPHATIDE-CONTAINING MATRIX

BACKGROUND

Lecithin and lecithin fractionates are staple articles of commerce having a wide range of applications. Generally, lecithin of plant origin is obtained from soybeans by (i) cleaning the soybeans, (ii) crushing the soybeans, (iii) separating the crushed soybeans into soybean oil and soybean meal, and (iv) separating the soybean oil into a degummed soybean oil and lecithin.

Lecithin is a complex mixture of phosphatides, glycolipids, triglycerides, carbohydrates, free fatty acids, proteins, fibers and various other constituents of known and unknown structure. Various methods are known for purifying, modifying and fractionating lecithin to produce products containing enhanced concentrations of one or more of the phosphatides—such as phosphatidyl choline, phosphatidyl ethanol amine, phosphatidyl inositol, phosphatidyl serine and phosphatidic acid.

British patent 412 224 discloses treatment of lecithin with acetone or a mixture of acetone and an alkane solvent to selectively dissolve the triglycerides in the lecithin and thereby leave a phosphatide enriched oil-free insoluble fraction.

British patent 877 031 discloses treatment of lecithin with an alcohol for selectively dissolving phosphatidyl choline relative to other phosphatides in the lecithin and thereby producing a phosphatidyl choline enriched alcohol fraction. German patent 14 94 952 discloses that the phosphatidyl choline selectivity of this process can be improved by using aqueous alcohol, while German Patent 16 92 568 discloses that the phosphatidyl choline selectivity of this process can be improved by adding monoglycerides.

A further purified phosphatidyl choline product can be obtained from such a phosphatidyl choline enriched alcohol fraction by (i) treating the phosphatidyl choline enriched alcohol fraction with an adsorbent—such as aluminum oxide—for selectively adsorbing and removing phosphatidyl ethanol amine from the alcohol fraction (British patent 877 031), (ii) treating the phosphatidyl choline enriched alcohol fraction with acetic acid anhydride to convert acetone insoluble phosphatidyl ethanol amine in the alcohol fraction to acetone soluble acetylphosphatidylamine, followed by treatment of the fraction with acetone for selectively dissolving the acetylphosphatidylamine relative to the phosphatidyl choline and thereby producing a phosphatidyl choline enriched solids fraction (British patents 1 217 846 and 1 350 390), and (iii) treating the phosphatidyl choline enriched alcohol fraction with a bivalent or trivalent metal salt, such as magnesium sulfate, to selectively precipitate phosphatidyl ethanol amine from the alcohol fraction (EP patent 0 090 454).

While generally effective for producing a phosphatide and/or phosphatidyl choline enriched lecithin fraction, these processes involve an excessive number of processing steps and typically produce a low yield of the desired product. Hence, a continuing need exists for a simple and efficient method of selectively extracting individual phosphatides or mixtures of phosphatides from a phosphatide-containing matrix at high yield.

SUMMARY OF THE INVENTION

A first embodiment of the invention is a process for releasing and extracting phosphatides from a phosphatide-containing matrix. The process includes (i) contacting the phosphatide-containing matrix with a solvent and a metal salt to release phosphatides from the matrix and form a phosphatide enriched solvent portion and a phosphatide depleted matrix portion, (ii) separating the phosphatide enriched solvent portion from the phosphatide depleted matrix portion, and (iii) recovering the phosphatides from the phosphatide enriched solvent portion.

A second embodiment of the invention is a process for releasing and extracting phosphatides from a phosphatide-containing matrix which has not been contacted with hexane. The process includes (i) contacting the phosphatide-containing matrix with a solvent and a metal salt to release phosphatides from the matrix and form a phosphatide enriched solvent portion and a phosphatide depleted matrix portion, wherein the solvent is a $C_{1-3}$ alcohol or combination of a $C_{1-3}$ alcohol and water, (ii) separating the phosphatide enriched solvent portion from the phosphatide depleted matrix portion, and (iii) recovering the phosphatides from the phosphatide enriched solvent portion, thereby producing a hexane-free phosphatide product.

DETAILED DESCRIPTION OF THE INVENTION INCLUDING A BEST MODE

Definitions

As utilized herein, including the claims, the term "depleted" means lessened in quantity or content.

As utilized herein, including the claims, the term "enriched" means increased in quantity or content.

As utilized herein, including the claims, the term "light metal" encompasses the alkali metals and alkaline earth metals.

As utilized herein, including the claims, the phrase "phosphatide-containing matrix" means a solid mass of ethanol insoluble material containing at least one embedded phosphatide.

As utilized herein, including the claims, the term "selective" means to take by preference so as to increase the percentage of the selected object(s), item(s) or thing(s) in the selected portion.

Compounds Used in the Process

The invention is a process for releasing and extracting phosphatides from a phosphatide-containing matrix with an initial step of contacting the phosphatide-containing matrix with a solvent and a metal salt to form a matrix-containing mixture, release phosphatides from the matrix and form a phosphatide enriched solvent portion and a phosphatide depleted matrix portion.

Phosphatides are a group of organic compounds consisting of an alcohol (usually glycerol), combined with fatty acids, phosphoric acid, and a nitrogen-containing compound. Phosphatides of commercial interest include phosphatidyl choline, phosphatidyl inositol, phosphatidyl ethanol amine, phosphatidyl serine, and phosphatidic acid. Phosphatides are present in significant concentrations in vegetable oils and lecithin, particularly soybean oil and lecithin obtained from soybeans. Lecithin obtained from soybeans typically contains about 14 wt % phosphatidyl choline, about 10 wt % phosphatidyl inositol, about 10 wt % phosphatidyl ethanol amine and about 4 wt % phosphatidic acid. A preferred phosphatide-containing matrix for use in the process of this invention is de-oiled lecithin obtained from soybeans.

Phosphatides are soluble in many organic polar solvents, including specifically but not exclusively alcohols and DMSO, and supercritical $CO_2$. The invention preferably uses a $C_{1-3}$ alcohol or a combination of a $C_{1-3}$ alcohol and water as such alcohols are safer and easier to use than most other organic polar solvents.

We have surprisingly discovered that addition of a metal salt to a phosphatide-containing matrix along with a polar solvent can significantly increase the amount of phosphatides released from the matrix into the solvent. Preferred metal salts are the light metal chlorides, light metal hydroxides and light metal sulfates, with a modest preference for calcium, sodium and magnesium sulfates.

We have discovered that phosphatidyl choline and phosphatidyl ethanol amine can be selectively separated from other phosphatides—particularly phosphatidic acid—in a phosphatide-containing matrix by adjusting the pH of the matrix-containing mixture—when necessary—to a pH of greater than 8 utilizing a pH adjustment agent. Substantially any of the well-known and widely available pH adjustment agents effective for increasing or decreasing the pH of such a mixture—dependant upon the starting pH of the matrix-containing mixture—can be employed, including specifically but not exclusively bases such as calcium carbonate or sodium hydroxide, and acids such as citric acid or phosphoric acid.

We have similarly discovered that phosphatidic acid can be selectively separated from other phosphatides—particularly phosphatidyl inositol—in a phosphatide-containing matrix by adjusting the pH of the matrix-containing mixture to a pH of less than 5 utilizing a pH adjustment agent.

Process

The invention is a process for releasing and extracting phosphatides from a phosphatide-containing matrix. The process includes (i) contacting the phosphatide-containing matrix with a solvent and a metal salt to release phosphatides from the matrix and form a phosphatide enriched solvent portion and a phosphatide depleted matrix portion, (ii) separating the phosphatide enriched solvent portion from the phosphatide depleted matrix portion, and (iii) recovering the phosphatides from the phosphatide enriched solvent portion.

The phosphatide-containing matrix can be blended with a solvent and a metal salt by any of the well-known means capable of providing an intimate mixture of a solid and a liquid. Suitable processes and systems include specifically, but not exclusively, batch percolators, continuous percolators, batch stirred tanks, continuous-flow stirred tanks, single screw and double-screw extruders, continuous dispersed-solids leaching towers, screw-conveyor extractors, etc. A preferred method is to add the metal salt to the solvent—along with any desired pH adjustment agent—under sufficient agitation to suspend the metal salt in the solvent, then adding the phosphatide-containing matrix to the solvent under sufficient agitation to suspend the phosphatide-containing matrix in the solvent, and then feeding the mixture into a high-shear, two-stage continuous blender.

Generally, the phosphatide-containing matrix should be contacted with solvent and metal salt at a matrix to solvent (g to ml) ratio between 1:1 and 1:10, preferably between 1:3 and 1:5, and a matrix to metal salt weight ratio between 2:1 and 10:1, preferably between 4:1 and 7:1.

Contacting the phosphatide-containing matrix, solvent and metal salt as set forth above results in a phosphatide enriched solvent portion and a phosphatide depleted matrix portion. These portions then need to be separated. Separation of the phosphatide enriched solvent portion and a phosphatide depleted matrix portion can be achieved by any of the well-known solid-liquid separation techniques. Suitable processes and systems include specifically, but not exclusively, decantation, countercurrent decantation, gravity sedimentation, filtration, expression, centrifugation and combinations thereof. The preferred method is centrifugation.

The phosphatides in the phosphatide enriched solvent portion can then be recovered from the solvent by any of the well-known techniques for separating a solute and/or suspended solids from a solvent including specifically, but not exclusively, adsorption, ambient evaporation, filtration, precipitation, drying-such as drum-drying, spray-drying and vacuum drying-and combinations thereof. The preferred method is a heated evaporator equipped with a condenser.

In a most preferred embodiment of the invention, the phosphatide-containing matrix used in the process has not been contacted with hexane prior to being processed in accordance with the invention, and is not contacted with hexane during the entire process so as to produce a completely hexane-free phosphatide product.

EXAMPLES

Glossary

| ACRONYM | DESCRIPTION |
| --- | --- |
| N-acyl PE | N-acylphosphatidyl ethanol amine |
| PA | Phosphatidic acid |
| PE | Phosphatidyl ethanol amine |
| PC | Phosphatidyl choline |
| PI | Phosphatidyl inositol |
| LPC | Lysophosphatidyl choline |

Example 1

Dry deoiled lecithin obtained from soybeans was analyzed with a High Performance Liquid Chromatograph according to a combination of AOCS Methods Ca19-97 and Ja7b-97 wherein all the components are separated by eluting them from an HPLC diol-column and determined with an evaporative light scattering detector (hereinafter referenced as the "Combination Testing Protocol"). The concentration of each phospholipid in the deoiled lecithin is set forth in TABLE ONE.

Into a jacketed tank equipped with an agitator and a heater, was placed 4,400 kg of the dry deoiled lecithin and 704 kg of sodium sulfate obtained from a commercial supplier. The lecithin and sodium sulfate were blended together to form a dry mix. Anhydrous ethanol at −5° C. was added to the dry mix at a ratio of 4.1:1 ethanol to dry mix under vigorous mixing to form a solvent mixture. The temperature of the solvent mixture rose to 25° C. and was maintained under constant agitation for three to five minutes. The agitated solvent mixture was then poured into a decanting centrifuge and the solvent portion separated from the solids portion. The separated solvent portion was concentrated to $\frac{1}{10}^{th}$ the original volume by evaporation and the concentrate vacuum dried to a moisture/volatile content of about 3 wt % to yield 717.2 kg of vacuum dried concentrate (16.3% of the dry deoiled lecithin). The composition of the vacuum dried concentrate was analyzed with the High Performance Liquid Chromatograph according to the Combination Testing Protocol. The concentration of each phospholipid in the vacuum dried concentrate is set forth in TABLE ONE. The vacuum dried concentrate contained about 113 ppm sodium. The solids portion was found to contain about 2,100 ppm sodium.

As shown in TABLE ONE, total phosphatides, PC and PA were selectively released, extracted and concentrated in the ethanol.

The extraction procedure was repeated using 100 g of the solids portion from the first extraction procedure without adding any additional sodium sulfate. The moisture/volatile content of the vacuum dried second concentrate was not recorded. The second extraction yielded 11.3 g of vacuum dried concentrate (11.3% of the solids portion from the first extraction procedure).

The composition of the second vacuum dried concentrate was analyzed with the High Performance Liquid Chromatograph according to the Combination Testing Protocol. The concentration of each phospholipid in the second vacuum dried concentrate is set forth in TABLE ONE. The second vacuum dried concentrate contained about 115 ppm sodium.

As shown in TABLE ONE, total phosphatides, PC and PA were once again selectively released, extracted and concentrated in the ethanol.

The extraction procedure was repeated a third time using 100 g of the solids portion from the second extraction procedure without adding any additional sodium sulfate. The third concentrate was vacuum dried to a moisture/volatile content of about 4.1 wt % to yield 6.75 g of vacuum dried concentrate (6.75% of the solids portion from the second extraction procedure).

The composition of the third vacuum dried concentrate was analyzed with the High Performance Liquid Chromatograph according to the Combination Testing Protocol. The concentration of each phospholipid in the third vacuum dried concentrate is set forth in TABLE ONE. The third vacuum dried concentrate contained about 181 ppm sodium.

As shown in TABLE ONE, total phosphatides, PC, PA and PE were selectively released, extracted and concentrated in the ethanol.

TABLE ONE

| Component | First Extraction Lecithin (wt %) | First Extraction Solvent Fraction (wt %) | Second Extraction Once Extracted Lecithin (wt %) | Second Extraction Solvent Fraction (wt %) | Third Extraction Solvent Fraction (wt %) |
|---|---|---|---|---|---|
| N-acyl PE | 1.85 | 5.2 | 1.24 | 4.00 | 4.47 |
| PA | 4.11 | 8.97 | 3.76 | 8.97 | 14.78 |
| PE | 20.51 | 18.02 | 19.0 | 21.51 | 31.95 |
| PC | 24.47 | 53.28 | 13.3 | 47.9 | 37.48 |
| PI | 13.27 | 1.37 | 12.5 | 1.92 | 1.55 |
| LPC | 0.5 | 1.86 | 0.36 | 1.27 | 0.97 |
| TOTAL | 64.71 | 88.7 | 50.2 | 85.57 | 91.20 |

Example 2

A semi-liquid crude lecithin obtained from soybeans was analyzed with a High Performance Liquid Chromatograph according to a combination of AOCS Methods Ca19-97 and Ja7b-97 wherein all the components are separated by eluting them from an HPLC diol-column and determined with an evaporative light scattering detector (hereinafter referenced as the "Combination Testing Protocol"). The concentration of each phospholipid in the crude lecithin is set forth in TABLE TWO.

Into a beaker equipped with a POLYTRON™ high sheer mixer was placed 100 g of the dry crude lecithin, 20 g of sodium sulfate obtained from a commercial supplier and 400 g acetone to form a solvent mixture. The solvent mixture was maintained under constant agitation for 4 minutes. The agitated solvent mixture was then poured into a centrifugal bottle and centrifuged for 15 minutes at 5,000 rpm. The solvent portion was then decanted from the solids portion and the solids portion dried under vacuum to form a once acetone-deoiled solids portion.

The extraction procedure was repeated using the once acetone-extracted solids portion—without adding any additional sodium sulfate—to form a twice acetone-deoiled solids portion.

The twice acetone-deoiled solids portion and 400 g of anhydrous ethanol were placed into a beaker equipped with a POLYTRON™ high sheer mixer to form a solvent mixture. The solvent mixture was maintained under constant agitation for 4 minutes. The agitated solvent mixture was then poured into a centrifugal bottle and centrifuged for 15 minutes at 5,000 rpm. The solvent portion was then decanted from the solids portion and the solvent portion vacuum dried to yield 17.51 g of concentrate (17.51% of the dry crude lecithin).

The composition of the vacuum dried alcohol-extracted concentrate was analyzed with the High Performance Liquid Chromatograph according to the Combination Testing Protocol. The concentration of each phospholipid in the vacuum dried alcohol-extracted concentrate is set forth in TABLE TWO.

As shown in TABLE TWO, total phosphatides, PC, PA and PE were selectively released, extracted and concentrated in the ethanol while the concentration of PI is significantly reduced.

TABLE TWO

| Component | Lecithin (wt %) | Ethanol Fraction (wt %) | % Change |
|---|---|---|---|
| N-acyl PE | 1.1 | 3.85 | +350% |
| PA | 4.2 | 10.96 | +161% |
| PE | 10.2 | 13.27 | +30% |
| PC | 14.0 | 49.04 | +250% |
| PI | 10.0 | 1.61 | −84% |
| LPC | 0.53 | 1.85 | +349% |
| TOTAL[#] | 38.40 | 74.88 | +95% |

[#]TOTAL of Ethanol Fraction excludes N-acyl PE and LPC to permit a direct comparison of the TOTAL % of phosphatides in the Lecithin and Ethanol Fraction.

Example 3

Dry deoiled lecithin obtained from soybeans was analyzed with a High Performance Liquid Chromatograph according to a combination of AOCS Methods Cal 9-97 and Ja7b-97 wherein all the components are separated by eluting them from an HPLC diol-column and determined with an evaporative light scattering detector (hereinafter referenced as the "Combination Testing Protocol"). The concentration of each phospholipid in the deoiled lecithin is set forth in TABLE THREE.

Into a ribbon blender, was placed 643 kg of the dry deoiled lecithin and 102 kg of sodium sulfate obtained from a commercial supplier. The lecithin and sodium sulfate were blended together to form a dry mix. The dry mix was then placed into a jacketed vessel equipped with an agitator and ethanol at −5° C. was added to the dry mix at a ratio of 4.1:1 ethanol to dry mix under vigorous agitation to form a solvent mixture. The temperature of the solvent mixture rose to 25° C. and was maintained under constant agitation for three to five minutes. The agitated solvent mixture was then run through an inline mixer and dumped into a decanting centrifuge where the solvent portion was separated from the solids portion. The separated solvent portion was concentrated by evaporation and the concentrate vacuum dried to a moisture/volatile content of about 2.8 wt % to yield 130 kg of vacuum dried concentrate (20.2% of the original dry deoiled lecithin). The composition of the vacuum dried concentrate was analyzed with the High Performance Liquid Chromatograph according to the Combination Testing Protocol. The concentration of each phospholipid in the vacuum dried concentrate is set forth in TABLE THREE. The vacuum dried concentrate contained about 69.8 ppm sodium.

As shown in TABLE THREE, total phosphatides, PC and PA were selectively released, extracted and concentrated in the ethanol.

The extraction procedure was repeated using the solids portion from the first extraction procedure (796 kg containing approximately 32% moisture/volatiles) without adding any additional sodium sulfate. The second extraction yielded 74.4 kg of vacuum dried concentrate (11.6% of the original dry deoiled lecithin) with a moisture/volatile content of about 2.77 wt %.

The composition of the second vacuum dried concentrate was analyzed with the High Performance Liquid Chromatograph according to the Combination Testing Protocol. The concentration of each phospholipid in the second vacuum dried concentrate is set forth in TABLE THREE. The second vacuum dried concentrate contained about 99.6 ppm sodium.

As shown in TABLE THREE, total phosphatides, PC and PA were once again selectively released, extracted and concentrated in the ethanol.

The extraction procedure was repeated a third time using the solids portion from the second extraction procedure (631 kg containing approximately 32% moisture/volatiles) without adding any additional sodium sulfate. The third extraction yielded 30.9 kg of vacuum dried concentrate (4.8% of the original dry deoiled lecithin) with a moisture/volatile content of about 2.56 wt %.

The composition of the third vacuum dried concentrate was analyzed with the High Performance Liquid Chromatograph according to the Combination Testing Protocol. The concentration of each phospholipid in the third vacuum dried concentrate is set forth in TABLE THREE. The third vacuum dried concentrate contained about 150 ppm sodium.

The concentration of each phospholipid in the fully spent biomass was analyzed in accordance with the "Combination Testing Protocol". The concentration of each phospholipid in the fully spent biomass is set forth in TABLE THREE.

As shown in TABLE THREE, total phosphatides, PC, PA and PE were selectively released, extracted and concentrated in the ethanol.

TABLE THREE

| Component | Lecithin (wt %) | First Solvent Fraction (wt %) | Second Solvent Fraction (wt %) | Third Solvent Fraction (wt %) | Spent Biomass (wt %) |
|---|---|---|---|---|---|
| N-acyl PE | 1.85 | 4.00 | 3.96 | 4.02 | Below Detectable Levels |
| PA | 4.11 | 6.01 | 7.3 | 10.0 | Below Detectable Levels |
| PE | 20.51 | 14.1 | 22.1 | 26.1 | 7.73 |
| PC | 24.47 | 55.6 | 51.9 | 40.4 | 1.43 |
| PI | 13.27 | 0.57 | 1.32 | 1.74 | 10.16 |
| LPC | 0.5 | 1.32 | 1.73 | 1.02 | Below Detectable Levels |
| TOTAL | 64.71 | 81.6 | 88.3 | 83.3 | 19.32 |

We claim:

1. A process for releasing and extracting phosphatides from a phosphatide-containing matrix comprising:
    (a) contacting the phosphatide-containing matrix with a solvent and a metal salt at a matrix to metal salt weight ratio between 2:1 and 10:1 to release phosphatides from the matrix and form a phosphatide enriched solvent portion and a phosphatide depleted matrix portion,
    (b) separating the phosphatide enriched solvent portion from the phosphatide depleted matrix portion, and
    (c) recovering the phosphatides from the phosphatide enriched solvent portion.

2. The process of claim 1 wherein the phosphatides released and extracted by the process include at least phosphatidyl choline.

3. The process of claim 1 wherein the phosphatides released and extracted by the process include at least phosphatidyl inositol.

4. The process of claim 1 wherein the phosphatides released and extracted by the process include at least phosphatidyl ethanol amine.

5. The process of claim 1 wherein the phosphatides released and extracted by the process include at least phosphatidyl serine.

6. The process of claim 1 wherein the phosphatides released and extracted by the process include at least phosphatidic acid.

7. The process of claim 1 wherein the phosphatide-containing matrix is derived from soybeans.

8. The process of claim 7 wherein the phosphatide-containing matrix is a de-oiled lecithin extract from soybeans.

9. The process of claim 1 wherein the phosphatide-containing matrix includes at least phosphatidyl choline, phosphatidyl ethanol amine and one other phosphatide and the phosphatide-containing matrix is contacted with solvent and a metal salt at a pH of greater than 8 whereby the phosphatidyl choline and phosphatidyl ethanol amine are selectively separated from the at least one other phosphatide.

10. The process of claim 1 wherein the phosphatide-containing matrix includes at least phosphatidic acid and one other phosphatide and the phosphatide-containing matrix is contacted with solvent and a metal salt at a pH of less than 5 whereby the phosphatidic acid is selectively separated from the at least one other phosphatide.

11. The process of claim 10 wherein the one other phosphatide is phosphatidyl inositol.

12. The process of claim 1 wherein the solvent is selected from a polar solvent.

13. The process of claim 12 wherein the solvent is a $C_{1-3}$ alcohol or a combination of a $C_{1-3}$ alcohol and water.

14. The process of claim 1 wherein the metal salt is a light metal chloride, light metal hydroxide or light metal sulfate.

15. The process of claim 14 wherein the metal salt is a light metal sulfate.

16. The process of claim 15 wherein the light metal sulfate is calcium, sodium or magnesium sulfate.

17. The process of claim 1 wherein the phosphatide-containing matrix is contacted with solvent at a matrix to solvent (g to ml) ratio between 1:1 and 1:10.

18. The process of claim 1 wherein the phosphatide-containing matrix is contacted with solvent at a matrix to solvent (g to ml) ratio between 1:3 and 1:5.

19. The process of claim 1 wherein the phosphatide enriched solvent portion is separated from the phosphatide depleted matrix portion by centrifugation.

20. The process of claim 1 wherein the phosphatide-containing matrix is counter-currently contacted with the solvent and metal salt.

21. The process of claim 1 herein phosphatides are recovered from the phosphatide enriched solvent portion by evaporation of solvent or precipitation of a phosphatide enriched precipitate from the phosphatide enriched solvent portion and separation of the precipitate from the liquid phase by centrifugation or filtration.

22. The process of claim 21 wherein phosphatides are recovered from the phosphatide enriched solvent portion by evaporation of solvent.

* * * * *